(12) United States Patent
Stephanopoulos et al.

(10) Patent No.: US 10,174,347 B2
(45) Date of Patent: Jan. 8, 2019

(54) METHOD FOR PRODUCING LACTIC ACID FROM ORGANIC WASTE

(71) Applicant: Massachusetts Institute of Technology, Cambridge, MA (US)

(72) Inventors: Gregory Stephanopoulos, Winchester, MA (US); Devin Hedley Currie, Somerville, MA (US); Kristen Jean Fortnam, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/142,877

(22) Filed: Apr. 29, 2016

(65) Prior Publication Data
US 2016/0355849 A1 Dec. 8, 2016

Related U.S. Application Data (60) Provisional application No. 62/154,802, filed on Apr. 30, 2015.

(51) Int. Cl.
 *C12P 7/56* (2006.01)
 *C12P 39/00* (2006.01)

(52) U.S. Cl.
 CPC ............... *C12P 7/56* (2013.01); *C12P 39/00* (2013.01)

(58) Field of Classification Search
None
See application file for complete search history.

(56) References Cited

U.S. PATENT DOCUMENTS

| | | | | |
|---|---|---|---|---|
| 5,135,861 A | * | 8/1992 | Pavilon | C12P 7/06 435/161 |
| 5,459,053 A | | 10/1995 | Rasmussen | |
| 5,506,123 A | | 4/1996 | Chieffalo et al. | |
| 7,098,009 B2 | | 8/2006 | Shanmugam et al. | |
| 8,492,127 B2 | | 7/2013 | Xu et al. | |

OTHER PUBLICATIONS

Leroy et al. (Trends in Food Science & Technology, vol. 15, 2004, pp. 67-78).*
Leven et al. (FEMS Microbiol. Eco., vol. 59, 2007, pp. 683-693).*
Abdel-Rahman et al., (J. of Biotech, vol. 156, 2011, pp. 286-301).*
[No Author Listed] Center for Sustainable Systems University of Michigan. 2016: Municipal Solid Waste Factsheet. Pub. No. CSS04-15. In.; 2014.
Alford, Bioprocess control: Advances and challenges. Computers & Chem Eng. Sep. 12, 2006;30(10-12):1464-75. http://doi.org/10.1016/j.compchemeng.2006.05.039.
Babel et al., Effect of acid speciation on solid waste liquefaction in an anaerobic acid digester. Water Research 2004, 38(9):2417-23. doi:10.1016/j.watres.2004.02.005.
Bachinger et al., Gas sensor arrays for early detection of infection in mammalian cell culture. Biosens Bioelectron. May 2002;17(5):395-403.
Bader, Sterilization: prevention of contamination. Manual of industrial microbiology and biotechnology. Eds.: Arnold L Demain and Nadine A Solomon. 1986;345-62.
Basílio et al., Detection and identification of wild yeast contaminants of the industrial fuel ethanol fermentation process. Curr Microbiol. Apr. 2008;56(4):322-6. doi: 10.1007/s00284-007-9085-5. Epub Jan. 8, 2008.
Bischoff et al., Modeling bacterial contamination of fuel ethanol fermentation. Biotechnol Bioeng. May 1, 2009;103(1):117-22. doi: 10.1002/bit.22244.
Brenner et al., Engineering microbial consortia: a new frontier in synthetic biology. Trends Biotechnol. Sep. 2008;26(9):483-9. doi:10.1016/j.tibtech.2008.05.004. Epub Jul. 31, 2008.
Buchholz et al., The roots—a short history of industrial microbiology and biotechnology. Appl Microbiol Biotechnol. May 2013;97(9):3747-62. doi:10.1007/s00253-013-4768-2. doi: 10.1007/s00253-013-4768-2. Epub Mar. 17, 2013.
Burmølle et al., Enhanced biofilm formation and increased resistance to antimicrobial agents and bacterial invasion are caused by synergistic interactions in multispecies biofilms. Appl Environ Microbiol. Jun. 2006;72(6):3916-23. doi:10.1128/AEM.03022-05.
Chen et al., Inhibition of anaerobic digestion process: a review. Bioresour Technol. Jul. 2008;99(10):4044-64. doi:10.1016/j.biortech.2007.01.057. Epub Mar. 30, 2007.
Cuellar et al., Large-scale production of diesel-like biofuels—process design as an inherent part of microorganism development. Biotechnol J. Jun. 2013;8(6):682-9. doi: 10.1002/biot.201200319. Epub May 6, 2013.
Datta et al., Lactic acid: recent advances in products, processes and technologies—a review. J Chem Technol Biotechnol 2006;81(7):1119-29. doi: 10.1002/jctb.1486.
Dearman et al., Methane production and microbial community structure in single-stage batch and sequential batch systems anaerobically co-digesting food waste and biosolids. Appl Microbiol Biotechnol. Jan. 2006;69(5):589-96. Epub Jul. 23, 2005. doi: 10.1007/s00253-005-0076-9.
Demirel, Major Pathway of Methane Formation From Energy Crops in Agricultural Biogas Digesters. Critical Reviews in Environmental Science and Technology. 2014; 44(3):199-222. doi: 10.1080/10643389.2012.710452.
Fernandez et al., Flexible community structure correlates with stable community function in methanogenic bioreactor communities perturbed by glucose. Appl Environ Microbiol. Sep. 2000;66(9):4058-67.
Fernando et al., Biorefineries: Current Status, Challenges, and Future Direction. Energy Fuels. 2006;20(4):1727-37. doi: 10.1021/ef060097w.
Jiang et al., Volatile fatty acids production from food waste: effects of pH, temperature, and organic loading rate. Bioresour Technol. Sep. 2013;143:525-30. doi:10.1016/j.biortech.2013.06.025. Epub Jun. 17, 2013.

(Continued)

*Primary Examiner* — Hope Robinson
(74) *Attorney, Agent, or Firm* — Wolf, Greenfield & Sacks, P.C.

(57) ABSTRACT

Aspects of the invention relate to methods for producing lactic acid from organic waste, comprising contacting organic waste with a microbial community to form a fermentation mixture, and fermenting the fermentation mixture under controlled pH and temperature conditions for a time sufficient to produce lactic acid.

18 Claims, 6 Drawing Sheets

(56) References Cited

OTHER PUBLICATIONS

Jones et al., Bacteriophage infections in the industrial acetone butanol (AB) fermentation process. J Mol Microbiol Biotechnol. Jan. 2000;2(1):21-6.

Junker et al., Sustainable reduction of bioreactor contamination in an industrial fermentation pilot plant. J Biosci Bioeng. Oct. 2006;102(4):251-68. doi: 10.1263/jbb.102.251.

Liu et al., The structure of the bacterial and archaeal community in a biogas digester as revealed by denaturing gradient gel electrophoresis and 16S rDNA sequencing analysis. J Appl Microbiol. Mar. 2009;106(3):952-66. doi:10.1111/j.1365-2672.2008.04064.x. Epub Jan. 30, 2009.

Łoś et al., Bacteriophage contamination: is there a simple method to reduce its deleterious effects in laboratory cultures and biotechnological factories? J Appl Genet. 2004;45(1):111-20.

Los, Minimization and prevention of phage infections in bioprocesses. Methods Mol Biol. 2012;834:305-15. doi: 10.1007/978-1-61779-483-4_19.

Manyi-Loh et al., Microbial anaerobic digestion (bio-digesters) as an approach for the decontamination of animal wastes in pollution control and the generation of renewable energy. Int J Environ Res Public Health. Sep. 17, 2013;10(9):4390-417. doi: 10.3390/ijerph10094390.

Marks et al., Bacteriophages and biotechnology: a review. J Chem Tech Biotech. Jan. 5, 2000;75(1):6-17.

Mccaskey et al., Bioconversion of Municipal Solid-Waste to Lactic-Acid by Lactobacillus Species. Appl Biochem Biotechnol. 1994;45-6:555-68. doi: 10.1007/bf02941830.

Muthaiyan et al., Antimicrobial strategies for limiting bacterial contaminants in fuel bioethanol fermentations. Progress Energy Combust Sci. 2011;37:351-70. doi:10.1016/j.pecs.2010.06.005.

Narihiro et al., Microbial communities in anaerobic digestion processes for waste and wastewater treatment: a microbiological update. Curr Opin Biotechnol. Jun. 2007;18(3):273-8. doi 10.1016/j.copbio.2007.04.003. Epub Apr. 25, 2007.

Negri et al., A Mathematical-Model of Volatile Fatty-Acids (VFA) Production in a Plug-Flow Reactor Treating The Organic Fraction of Municipal Solid-Waste (MSW). Wat Sci Tech 1993, 27(2):201-208.

Olson et al., Recent progress in consolidated bioprocessing. Curr Opin Biotechnol. Jun. 2012;23(3):396-405. doi:10.1016/j.copbio.2011.11.026. Epub Dec. 14, 2011.

Qian et al., Enumeration of anaerobic refuse-decomposing microorganisms on refuse constituents. Waste Manag Res. 1996, 14(2):151-61.

Qin et al., Non-sterilized fermentative production of polymer-grade L-lactic acid by a newly isolated thermophilic strain *Bacillus* sp. 2-6. PLoS One. 2009;4(2):e4359. doi: 10.1371/journal.pone.0004359. Epub Feb. 4, 2009.

Sharma et al., AK: Asepsis in Bioreactors. Advances in Applied Microbiology, vol. 39 1993, 39:1-27.

Supaphol et al., Microbial community dynamics in mesophilic anaerobic co-digestion of mixed waste. Bioresour Technol. Mar. 2011;102(5):4021-7. doi: 10.1016/j.biortech.2010.11.124. Epub Dec. 6, 2010.

Tsavkelova et al., Biogas production from cellulose-containing substrates: A review. Applied Biochemistry and Microbiology. 2012;48(5):421-433.

Wang et al., Producing hydrogen from wastewater sludge by Clostridium bifermentans. J Biotechnol. Apr. 10, 2003;102(1):83-92.

Warnecke et al., Organic acid toxicity, tolerance, and production in *Escherichia coli* biorefining applications. Microb Cell Fact. Aug. 25, 2005;4:25.

Watanabe et al., Fermentative $_L$-(+)-lactic acid production from non-sterilized rice washing drainage containing rice bran by a newly isolated lactic acid bacteria without any additions of nutrients. J Biosci Bioeng. Apr. 2013;115(4):449-52. doi: 10.1016/j.jbiosc.2012.11.001. Epub Nov. 28, 2012.

Yang et al., Lactic acid fermentation of food waste for swine feed. Bioresour Technol. Oct. 2006;97(15):1858-64. Epub Oct. 27, 2005.

Young, Sterilization of various diameter dead-ended tubes. Biotechnol Bioeng. Jun. 5, 1993;42(1):125-32.

Zheng et al., Problems with the microbial production of butanol. J Ind Microbiol Biotechnol. Sep. 2009;36(9):1127-38. doi: 10.1007/s10295-009-0609-9. Epub Jun. 27, 2009.

Zinder et al., Selective inhibition by 2-bromoethanesulfonate of methanogenesis from acetate in a thermophilic anaerobic digestor. Appl Environ Microbiol. Jun. 1984;47(6):1343-5.

PCT/US2016/030116, Jul. 28, 2016, International Search Report and Written Opinion.

\* cited by examiner

METHOD FOR PRODUCING LACTIC ACID
FROM ORGANIC WASTE

RELATED APPLICATIONS

This application claims the benefit under 35 U.S.C. § 119(e) of U.S. Provisional Application Ser. No. 62/154,802, entitled "METHODS FOR CONVERSION OF FOOD WASTE TO CHEMICAL PRODUCTS," filed on Apr. 30, 2015, the entire disclosure of which is herein incorporated by reference.

GOVERNMENT INTEREST

This invention was made with Government support under Grant No. DE-AR0000433 awarded by the Department of Energy. The Government has certain rights in the invention.

FIELD OF INVENTION

The invention relates to methods for producing lactic acid from organic waste using microbes.

BACKGROUND OF INVENTION

There is an increasing global demand for lactic acid. The U.S. is the largest consumer of lactic acid in the world, accounting for 45% of the total $22 billion per year market [43]. This high value chemical has applications in the food industry as an acidity regulator, preservative and flavoring agent, and in other industries such as pharmaceuticals, consumer goods, and recently in biodegradable plastics using its polymeric form—Poly Lactic Acid (PLA). With this wide array of uses, the lactic acid market is estimated to grow substantially, with a Compound Annual Growth Rate (CAGR) of 20% until at least 2019 [44].

SUMMARY OF INVENTION

Aspects of the invention relate to methods for producing lactic acid from organic waste, comprising contacting organic waste with a microbial community to form a fermentation mixture, and fermenting the fermentation mixture under controlled pH and temperature conditions for a time sufficient to produce lactic acid.

In some embodiments, the method does not comprise sterilization of the organic waste. In some embodiments, the method does not comprise enzyme addition to the fermentation mixture. In some embodiments, the organic waste is food waste or agricultural waste. In some embodiments, the microbial community comprises Firmicutes, *Bacteroides* and Spirochetes. In some embodiments, the microbial community further comprises hydrogenotrophic and acetoclastic archaeal methanogens.

In some embodiments, prior to fermentation, the organic waste is mechanically disrupted to a particle size of approximately 1 mm or smaller. In some embodiments, the mechanical disruption comprises shredding or grinding. In some embodiments, the solid content in the fermentation mixture is adjusted to 8-15%. In some embodiments, the pH is adjusted to at or below pH 6.0, optionally to between pH 5.0 to pH 6.0, optionally to about pH 5.5.

In some embodiments, the pH is adjusted by addition of sodium hydroxide or optionally other bases. In some embodiments, the temperature of the fermentation is about 37° C. In some embodiments, methods further comprise shifting the pH to between pH 3.86 and pH 4.75, inclusive, at or near the end of fermentation. In some embodiments, 60-100 grams of lactic acid per liter is produced.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. For purposes of clarity, not every component may be labeled in every drawing. In the drawings:

FIG. 5A shows that lactic acid begins to decrease after hour 60, with a commensurate increase in smaller short-chain fatty acids, whereas in FIG. 5B this does not occur.

DETAILED DESCRIPTION

The invention is based, at least in part, on the surprising discovery that the commodity chemical lactic acid can be effectively produced biologically from organic waste. Significantly, biological production through a controlled microbial community does not require sterilization or enzyme addition, in contrast to previous technologies. Methods described herein can produce crude lactic acid in the range of 60-100 grams per liter, which can be concentrated via a variety of methods known in the art. Organic waste, such as food waste, can be used as a feedstock and is available at a low cost (e.g., as low as $80/ton), making this a cost-effective approach.

Methods and compositions described herein will help fulfill the increasing global demand for lactic acid for use in a variety of industries including the food, cleaning, and polymer sectors. For example, one of the uses of lactic acid is in production of polylactic acid (PLA), which is a biodegradable thermoplastic with a growing number of applications as a result of its superior characteristics and green production method. Lactic acid produced using methods described herein will allow for even more cost-effective production of lactic acid and other related products, such as PLA.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Feedstock

Aspects of the invention relate to biological production of lactic acid from feedstock. As used herein, "feedstock" refers to any raw material that can be used to produce lactic acid. The feedstock can be organic waste. In some embodiments, the feedstock is organic municipal solid waste (MSW). In some embodiments, the feedstock is organic waste that has a high concentration of sugar, starch, and/or protein. For example, the organic waste can be food waste. In other embodiments, the feedstock is agricultural waste. It should be appreciated that the type of feedstock can influence the solid retention time in the incubator, such as a bioreactor. For example, for agricultural waste, the solid retention time in the bioreactor may increase to account for the recalcitrance of the material.

In other embodiments, biodegradable products, such as biodegradable dishes (e.g., plates or bowls) or biodegradable utensils (e.g., forks, spoons, or knives) that have been rated for biodegradability can be used as a feedstock. In some embodiments, retention times for such products may be longer than when using food waste as a feedstock.

Prior to fermentation, the feedstock, such as organic waste, can be mechanically disrupted (e.g., shredded or ground). In some embodiments, the feedstock, such as organic waste, is mechanically disrupted to a particle size of approximately 1 mm or smaller. For example, the particle size can be approximately 0.1 mm, 0.2 mm, 0.3 mm, 0.4 mm, 0.5 mm, 0.6 mm, 0.7 mm, 0.8 mm, 0.9 mm, or 1 mm, including any value in between. In some embodiments, the particle size is less than 0.1 mm. In some embodiments, the particle size is between 0.1-0.5 mm. In some embodiments, the particle size is between 0.5-1 mm. In some embodiments, the particle size is greater than 1 mm. The feedstock, such as organic waste, can be mechanically disrupted according to any means known in the art for mechanical disruption (e.g., with a grinder/shredder through which the food waste is passed).

Figure 1:
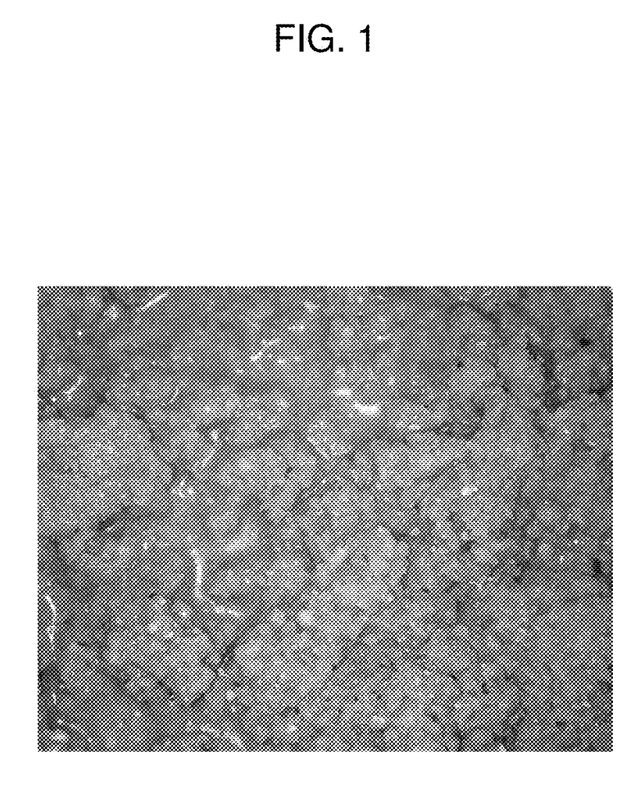
FIG. 1 depicts an example of processed feedstock in which the solid content is 20%, as determined by lyophilization. Food waste generally has a native water content of 80% which is then increased to 85-92% for fermentation to allow for robust mixing.
Figure 2:
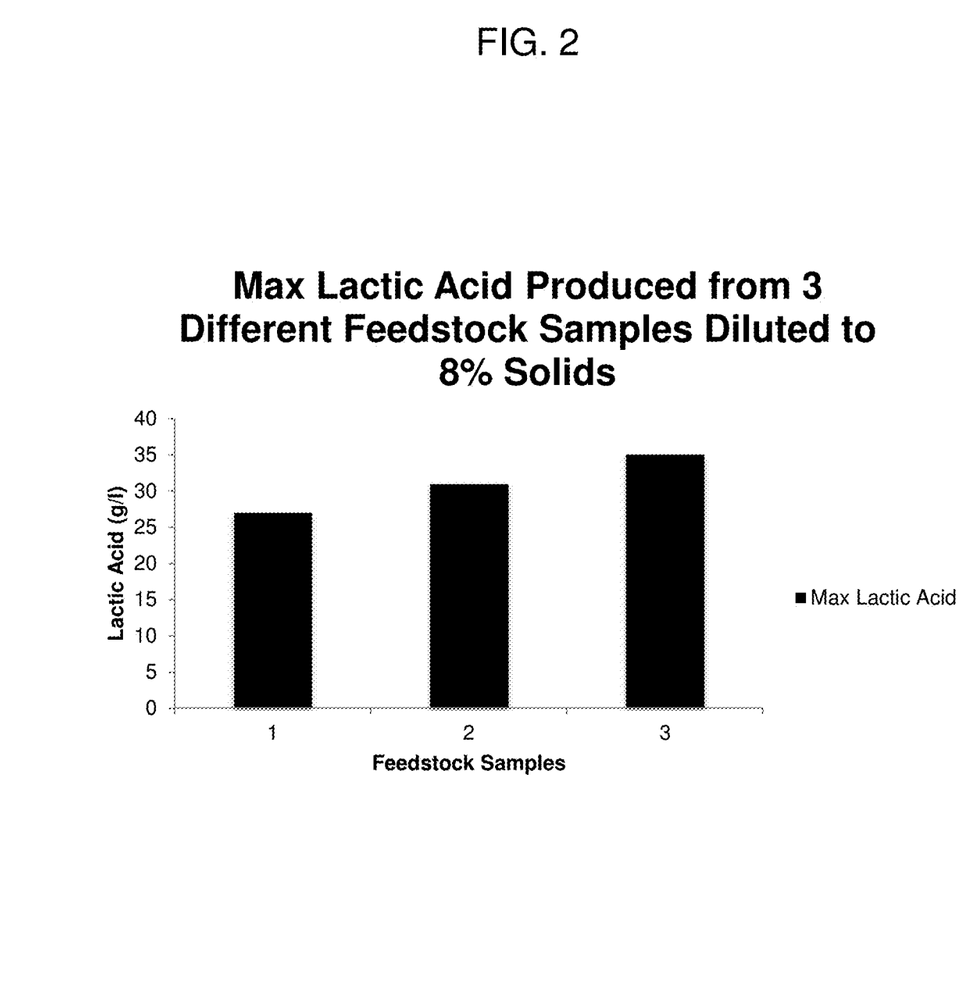
FIG. 2 depicts representative examples of maximum lactic acid production from three different food waste samples collected over a period of 6 months. The average amount of lactic acid produced in the three samples is 31 grams/liter (g/l), with a standard deviation of four.

Methods described herein can involve adjusting the solid content in the fermentation mixture. Food waste generally has a native water content of 80%. In some embodiments, the water content is increased to 85-92% for fermentation to allow for robust mixing. In some embodiments, the solid content is adjusted to 8-15%. For example, in some embodiments, the solid content is adjusted to approximately 8%, 9%, 10%, 11%, 12%, 13%, 14% or 15%. In some embodiments, the solid content is adjusted to less than 8%. For example, in some embodiments, the solid content is adjusted to approximately 1%, 2%, 3%, 4%, 5%, 6% or 7%. In some embodiments, the solid content is adjusted to above 15%. For example, in some embodiments, the solid content is adjusted to approximately 16%, 17%, 18%, 19%, 20%, 21%, 22%, 23%, 24% or 25%. In some embodiments, the solid content is adjusted to above 25%. In some embodiments, the solid content is determined by lyophilization. FIG. 1 shows an example of a processed feedstock with a solid content of 20%. FIG. 2 demonstrates lactic acid production from feedstock samples in which the solid content was adjusted to 8%.

Microbial Communities

Microbes have been used in a variety of fermentation processes in the past. For example, the yeast *Saccharomyces cerevisiae* has been used in beer and wine production [1]. However, process engineering challenges still exist for large scale fermentations [2-6]. For most industries employing microbes or other biocatalysts, sterilization remains a significant concern [7]. The feedstock and the bioreactor are both potential sources of contamination and are generally sterilized and monitored to avoid growth of contaminating phage [8-11], bacteria and fungi [12-15]. To maintain sterilization, various methods have been developed that require skilled personnel employing specialized equipment and strict standard operating procedures. These can include best practices, clean/steam in place sterilization for equipment, a pH range and medium design that favors the intended organism or community, and the addition of antibiotics [9, 11-13, 16-18]. All of these factors increase production overhead and may not ultimately be successful in creating sufficiently sterilized conditions. Contaminating microbes can decrease yield and/or titer of a final product, or produce compounds that result in the loss of a batch [19].

Traditional bioreactors frequently rely on a single organism. By contrast, bioreactors used for the fermentation of wastes, such as organic waste, including MSW, typically involve a consortium of microbes [20]. Consortia, unlike monocultures of single organisms, are less sensitive to the introduction of invading microbes and can more readily adapt to changing environmental conditions [21, 22]. This has been demonstrated at scale by the biogas industry, which is analogous in terms of reactor design and feedstock to the processes described herein [23, 24]. Methods of fermentation described herein involve communities or consortia of microbes. Accordingly, in some embodiments, for methods described herein, sterilization is unnecessary. In some embodiments, sterilization is undesirable. The ability to bypass sterilization leads to benefits associated with reductions in equipment and operation costs. In some embodiments, treatment with acid or enzymes to increase the digestibility of the material is also not required. Accordingly, in some embodiments, neither acid nor enzymes are added to the fermentation mixture to increase the digestibility of the material. A general process overview consistent with aspects of the invention is provided in FIG. 3. In some embodiments, methods can involve sterilization of at least one component of the bioreactor or fermentation process. In some embodiments, methods can involve treatment with acid or enzymes to increase digestibility of materials.

Aspects of the invention relate to conversion of organic waste, such as food waste, to lactic acid. In some embodiments, 0.5 tons of organic waste, such as food waste, is converted to crude lactic acid per day. In some embodiments, between 0.01-50 tons of organic waste, such as food waste, is converted to crude lactic acid per day. For example, in some embodiments, approximately 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.0, 1.5, 2.0, 2.5, 3.0, 3.5, 4.0, 4.5, 5.0, 5.5, 6.0, 6.5, 7.0; 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0; 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 tons of organic waste, such as food waste is converted to crude lactic acid per day.

Aspects of the invention relate to the use of microbes in anaerobic digestion of feedstock, such as organic waste. Communities responsible for anaerobic digestion are complex and have been extensively investigated [26-29]. In some embodiments, methods described herein use microbial communities comprising Firmicutes, *Bacteroides* and Spirochetes, optionally also including hydrogenotrophic and acetoclastic archaeal methanogens [30]. Unlike the process in which anaerobic digestion of MSW is used to produce methane via short-chain fatty acid intermediates, for the production of lactic acid, in some embodiments, the microbial community is shifted towards lactic acid producers and the methanogens are inhibited.

Figure 4:
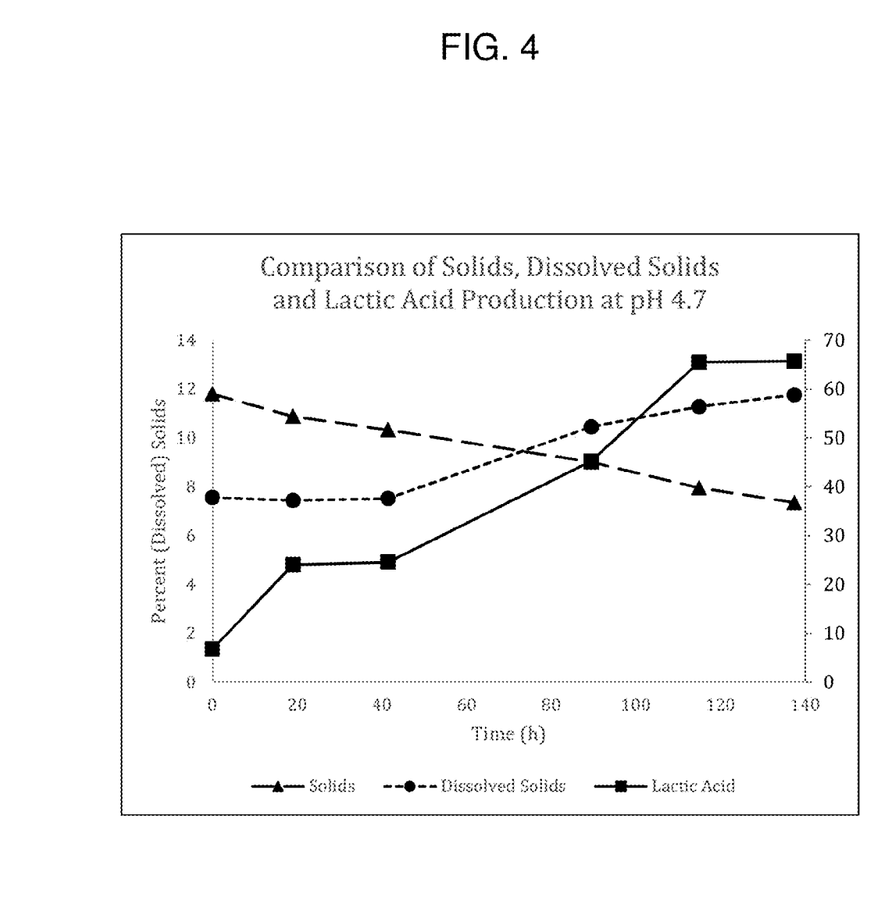
FIG. 4 depicts lactic acid production from food waste using a community of microbes commonly used in yogurt production. Comparisons are drawn between the solid content (as determined by centrifugation followed by lyophilization), dissolved solids (as determined by lyophilization) and lactic acid (as determined by HPLC).

During the growth phase, lactic acid accumulates and the solid content of the reactor decreases (although partially offset by cell mass accumulation) while the dissolved material increases. The dissolved material is almost entirely lactic acid (FIG. 4). The final solid material left over at the end of the process can be sold as a soil amendment akin to the sludge exiting a traditional biogas facility.

A wide variety of microbial communities are capable of catalyzing fermentation methods described herein and are compatible with aspects of the invention, including microbes used in yogurt production (FIG. 4). In some embodiments, one or more of the microbes is of the genus *Lactobacillus, Weissella, Streptococcus, Shewanella, Pediococcus, Leuconostoc,* or *Lactococcus*. In some embodiments, one or more of the microbes comprises *Lactobacillus delbrueckii, Lactobacillus amylovorus, Lactobacillus lactis, Lactobacillus casei, Lactobacillus acidophilus, Lactobacillus plantarum, Lactobacillus manihotivorans, Lactobacillus gasseri, Weissella cibaria, Weissella confuse, Weissella hellenica, Streptococcus equinus, Streptococcus infantarius* subsp. *Infantarius, Shewanella indica, Shewanella upenei, Pediococcus acidilactici, Pediococcus pentosaceus, Leuconostoc citreum, Leuconostoc lactis, Lactococcus lactic* ssp. *Lactis, Lactococcus garvieae*. Microbes can be identified using any means known in the art. In some embodiments, microbes can be identified using 16s sequencing of components of the fermentation mixture.

Aspects of the invention relate to the use of microbial communities within a fermentation mixture. In some embodiments, a fermentation mixture includes a community of microbes, feedstock, such as organic waste (e.g., food waste), and water. As one of ordinary skill in the art would appreciate, additional materials can be included within the fermentation mixtures.

Process Control

Aspects of the invention relate to controlling the fermentation process to achieve maximum lactic acid production with minimal unwanted side product formation. As one of ordinary skill in the art would appreciate, various aspects of the fermentation process can be controlled, such as pH and/or temperature. In some embodiments, the pH is controlled. In some embodiments, initial fermentation conditions are controlled at a pH of approximately 5.5. In some embodiment, the pH is controlled between 4.0-5.5. In some embodiments, the pH is controlled at or below 6.0. For example, in some embodiments, the pH is controlled at approximately 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0. It should be appreciated that any means known in the art can be used to control pH. For example, in some embodiments, to control pH, sodium hydroxide or other bases are added to neutralize the lactic acid and allow the continuation of robust growth and lactic acid production. In some embodiments, the base is sodium hydroxide. In some embodiments, the base is calcium hydroxide or calcium carbonate. In some embodiments, calcium lactate is included as a starting material for the distillation of lactic acid.

In some embodiments, the temperature is controlled to approximately 37° C. In some embodiments, the temperature is controlled to between 20-50° C. In some embodiments, the temperature is controlled to between 35-38° C. In some embodiments, the temperature is controlled to approximately 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

The timing of fermentation can also be controlled. In some embodiments, the fermentation time is between approximately 2.5-5 days. In some embodiments, the fermentation time is approximately 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 days. In some embodiments, the fermentation time is less than 2.5 days. In some embodiments, the fermentation time is less than 12 hours, 12-18 hours, 18-24 hours, 24-36 hours, or 36-48 hours. In some embodiments, the fermentation time is more than 5 days. In some embodiments, the fermentation time is 5, 6, 7, 8, 9, 10, 11, 12, 13, 14 days, or more than 14 days.

Aspects of the invention relate to production of lactic acid. Accordingly, in some embodiments, production of other products is minimized or reduced. Two downstream products that can be produced through more complete oxidation are methane and short-chain fatty acids like acetic acid. In some embodiments, production of methane and/or short-chain fatty acids like acetic acid is inhibited in order to maximize yields of lactic acid. In some embodiments, methanogenesis is abolished or reduced through any means known in the art. For example, in some embodiments, methanogenesis is abolished or reduced by adding chemicals that specifically inhibit archaeal methane production. For example, in some embodiments, 2-Bromoethanesulfonate is added [31]. In other embodiments, maintaining the bioreactor pH at or below pH 6.0 is sufficient to inhibit methanogenesis without the need for added chemicals [32].

In some embodiments, production of short-chain fatty acids is also reduced or abolished via pH control. Lactic acid has a pKa of 3.86, whereas acetic acid has a pKa of 4.75. Without wishing to be bound by any theory, when organic acids are in their undissociated state, they may be able to travel freely across the cell membrane, and once in the cytosol (which maintains a pH close to 7) they may be able to return to their acid form and poison the cell. In some embodiments, to inhibit production of acetic acid or other similar short chain fatty acids, pH is modulated. In some embodiments, pH is modulated via oscillations, a gradual shift, or an abrupt shift near the end of the fermentation. In some embodiments, pH is modulated to be below the pKA of acetic acid (4.75), but above the pKa of lactic acid (3.86), to kill microbes attempting to produce these undesirable compounds.

Figure 5A:
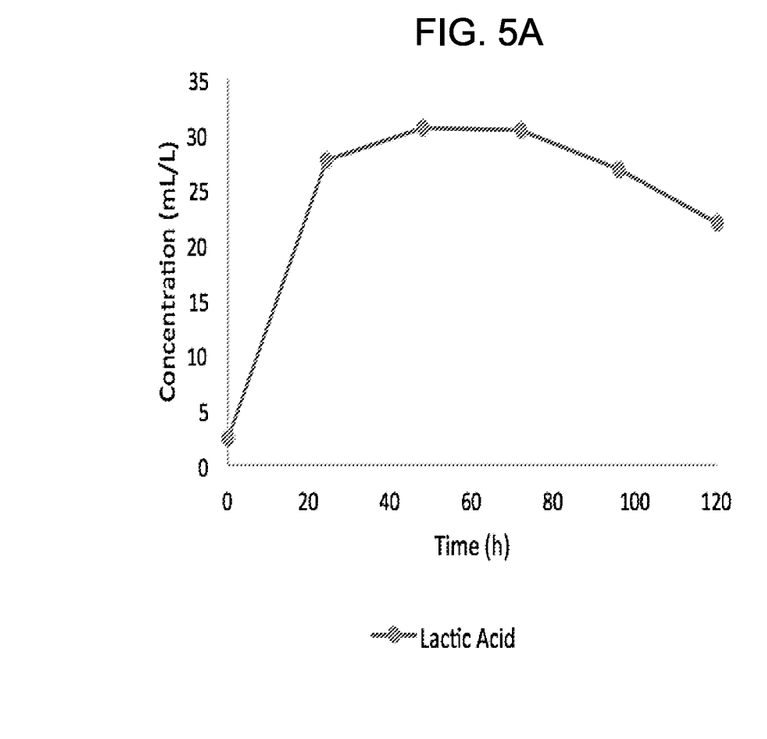
FIGS. 5A and 5B depict a comparison of pH controlled above the pKa of acetic acid (FIG. 5A) and below (FIG. 5B).
Figure 5B:
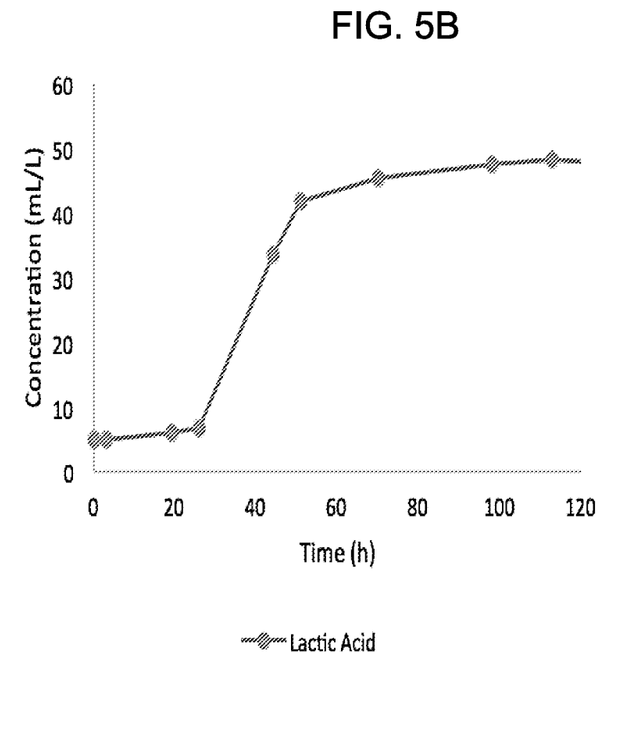

Accordingly, in some embodiments, the pH is shifted at or near the end of fermentation. In some embodiments, the pH is shifted to a lower pH. In some embodiments, the pH is shifted to a pH of between 3.86 and 4.75. For example, in some embodiments, the pH is shifted to approximately 3.86, 3.87, 3.88, 3.89, 3.90, 3.91, 3.92, 3.93, 3.94, 3.95, 3.96, 3.97, 3.98, 3.99, 4.00, 4.01, 4.02, 4.03, 4.04, 4.05, 4.06, 4.07, 4.08, 4.09, 4.10, 4.11, 4.12, 4.13, 4.14, 4.15, 4.16, 4.17, 4.18, 4.19, 4.20. 4.21, 4.22, 4.23, 4.24, 4.25, 4.26, 4.27, 4.28, 4.29, 4.30, 4.31, 4.32, 4.33, 4.34, 4.35, 4.36, 4.37, 4.38, 4.39, 4.40, 4.41, 4.42, 4.43, 4.44, 4.45, 4.46, 4.47, 4.48, 4.49, 4.50, 4.51, 4.52, 4.53, 4.54, 4.56, 4.57, 4.58, 4.59, 4.60, 4.61, 4.62, 4.63, 4.64, 4.65, 4.66, 4.67, 4.68, 4.69, 4.70, 4.71, 4.72, 4.73, 4.74, or 4.75. In methods described herein, pH control allows for elimination of toxicity presented by undissociated short-chain fatty acids leading to avoidance of unwanted side products [33, 34], and simultaneously allowing for inhibition of methanogenesis [20, 35, 36] (FIG. 5).

Methods described herein produce high yields of lactic acid. In some embodiments, 60-100 grams of lactic acid per liter is produced. For example, in some embodiments, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 grams of lactic acid per liter is produced. In some embodiments, more than 100 grams of lactic acid per liter is produced.

In some embodiments, 60-150 grams of lactic acid per kilogram of organic waste, such as food waste, is produced. For example, in some embodiments, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 grams of lactic acid per kilogram of organic waste, such as food waste, is produced. In some embodiments, more than 100 grams of lactic acid per kilogram of organic waste, such as food waste, is produced.

In some embodiments, 60-150 grams of lactic acid per ton of organic waste, such as food waste, is produced. For example, in some embodiments, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 grams of lactic acid per ton of organic waste, such as food waste, is produced. In some embodiments, more than 100 grams of lactic acid per ton of organic waste, such as food waste, is produced.

In some embodiments, about 70% of the dry matter is converted to lactic acid. In some embodiments, 1 kg of wet food waste corresponds to approximately 200 grams of dry matter when fermented and can produce at least 100 grams of lactic acid.

Methods described herein present significant advantages relative to existing methods, devices or materials for production of lactic acid. Previous production of lactic acid started with sugar, which can cost over $500/ton [37]. By contrast, methods described herein involve feedstocks that are much less expensive [38]. Previous methods also involved single microbes, defined feed stocks and treatment with acid or enzymes to increase the digestibility of the material by a defined microbe rather than a community [39, 41, 42]. By contrast, methods described herein involve a microbial community instead of individual microbes and do not require treatment with acid or enzymes to increase the digestibility of the material.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1: Production of Lactic Acid from Food Waste

Food waste was used as a source of feedstock. Prior to fermentation, the waste was mechanically disrupted (e.g., shredded or ground) to a particle size of approximately 1 mm or smaller. The solid content was adjusted down to 8-15% and the pH was adjusted to 5.5 (FIG. 1). FIG. 1 depicts an example of processed feedstock in which the solid content is 20% as determined by lyophilization.

Feedstock variability was not found to play a significant role in yield and titer of produced lactic acid (FIG. 2), even when the sample size is small (5 gallons). FIG. 2 depicts representative examples of maximum lactic acid production from 3 different food waste samples collected over the period of 6 months. The average of the 3 samples was 31 g/l, with a standard deviation of 4.

Figure 3:
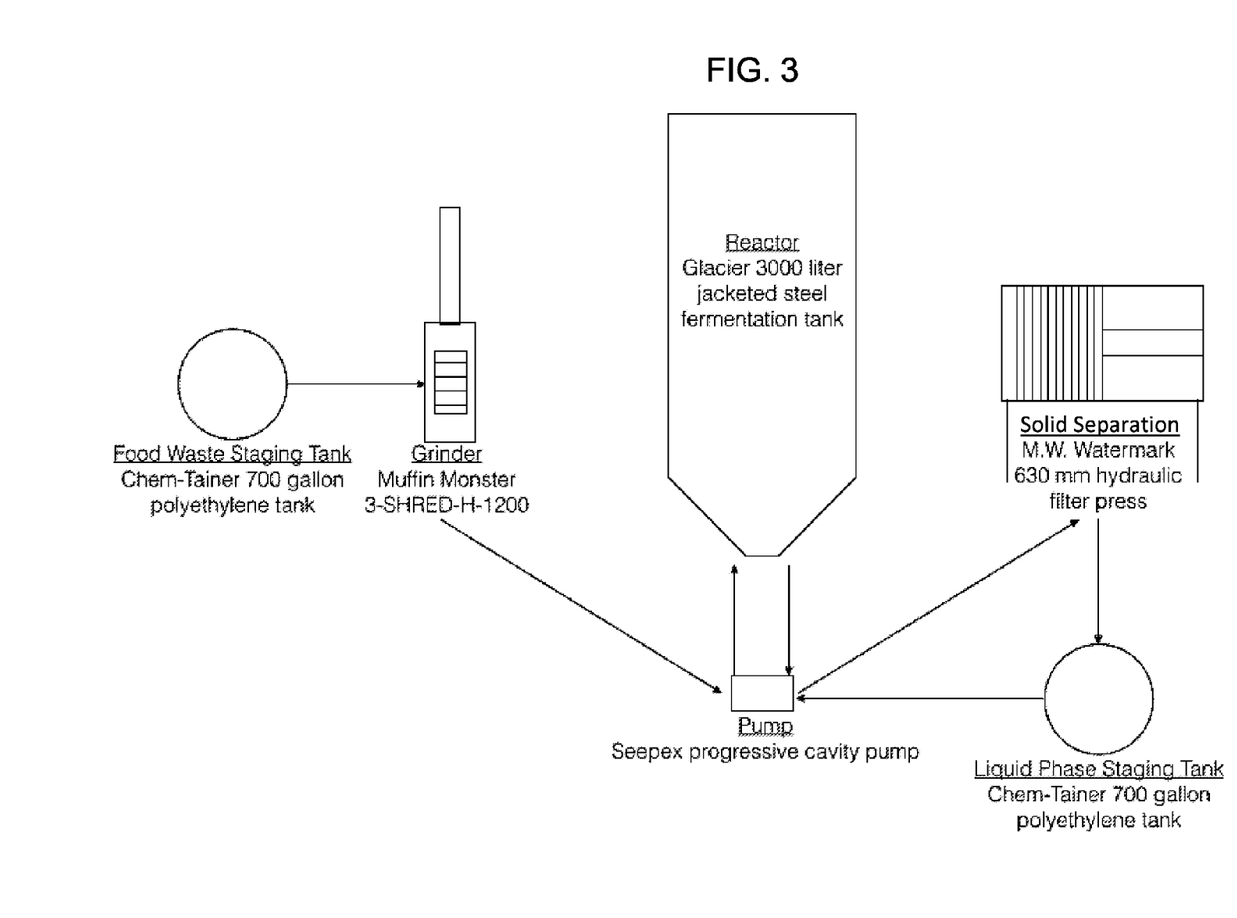
FIG. 3 depicts a small-scale process overview of a system to handle 0.5 tons of food waste per day for conversion to crude lactic acid.

FIG. 3 shows a small-scale process overview of a system to handle 0.5 tons of food waste per day for conversion to crude lactic acid. During the growth phase, lactic acid accumulates and the solid content of the reactor decreases (although partially offset by cell mass accumulation) while the dissolved material increases. The dissolved material is almost entirely lactic acid (FIG. 4). A wide variety of microbial communities are capable of catalyzing the process, including those used in yogurt production. FIG. 4 depicts lactic acid production from food waste using a community of microbes commonly used in yogurt production. Comparisons are drawn between the solid content (as determined by centrifugation followed by lyophilization), dissolved solids (as determined by lyophilization) and lactic acid (as determined by HPLC).

The process was controlled to achieve maximum lactic acid production with minimal unwanted side product formation. Initial fermentation conditions were controlled at pH 5.5 and a temperature of 37° C. To control pH, sodium hydroxide was added to neutralize the lactic acid and allow the continuation of robust growth and lactic acid production.

pH control allowed for inhibition of methanogenesis (FIG. 5). Employing these methods produced total yields of over 100 g/kilogram food waste. FIG. 5 depicts a comparison of pH controlled above the pKa of acetic acid (A) and below (B). In panel A, lactic acid begins to decrease after hour 60, with a commensurate increase in smaller short-chain fatty acids, whereas in B this does not occur. Higher titers were achieved in the reactor where no lactic acid consumption was possible.

Figure 6:
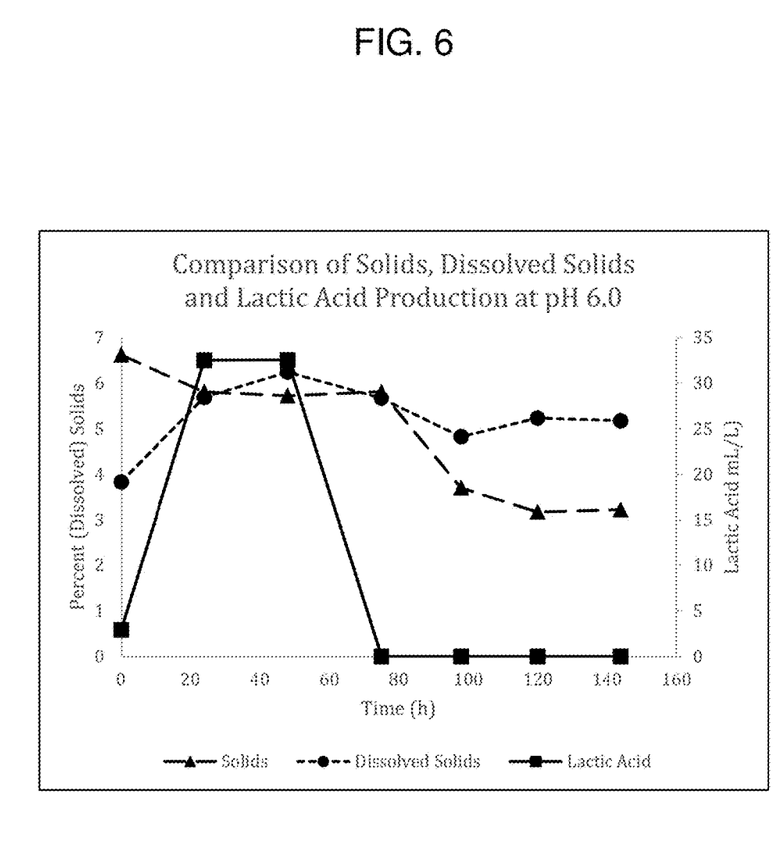
FIG. 6 depicts lactic acid production by a microbial community with pH held at 6.0. Comparisons are drawn between the solid content (as determined by centrifugation followed by lyophilization), dissolved solids (as determined by lyophilization) and lactic acid (as determined by HPLC).

When the pH was raised even higher to the traditional range for lactic acid production, lactic acid was consumed by the community nearly as fast as it is produced, disappearing in less than 48 hours (FIG. 6). FIG. 6. depicts lactic acid production by a microbial community with pH held at 6.0. Comparisons are drawn between the solid content (as determined by centrifugation followed by lyophilization), dissolved solids (as determined by lyophilization) and lactic acid (as determined by HPLC).

REFERENCES

1. Buchholz K, Collins J: The roots—a short history of industrial microbiology and biotechnology. *Appl Microbiol Biotechnol* 2013, 97(9):3747-3762.
2. Cuellar M C, Heijnen J J, van der Wielen L A: Large-scale production of diesel-like biofuels—process design as an inherent part of microorganism development. *Biotechnol J* 2013, 8(6):682-689.
3. Olson D G, McBride J E, Shaw A J, Lynd L R: Recent progress in consolidated bioprocessing. *Curr Opin Biotechnol* 2012, 23(3):396-405.
4. Zheng Y N, Li L Z, Xian M, Ma Y J, Yang J M, Xu X, He D Z: Problems with the microbial production of butanol. *J Ind Microbiol Biotechnol* 2009, 36(9):1127-1138.
5. Fernando S, Adhikari S, Chandrapal C, Murali N: Biorefineries: Current status, challenges, and future direction. *Energy & Fuels* 2006, 20(4):1727-1737.
6. Alford J S: Bioprocess control: Advances and challenges. *Computers & Chemical Engineering* 2006, 30(10-12):1464-1475.
7. Basillo A C M, de Araujo P R L, de Morais J O F, de Silva E A, de Morais M A, Simoes D A: Detection and identification of wild yeast contaminants of the industrial fuel ethanol fermentation process. *Current Microbiology* 2008, 56(4):322-326.
8. Jones D T, Shirley M, Wu X, Keis S: Bacteriophage infections in the industrial acetone butanol (AB) fermentation process. *J Mol Microbiol Biotechnol* 2000, 2(1):21-26.
9. Los M: Minimization and Prevention of Phage Infections in Bioprocesses. *Microbial Metabolic Engineering: Methods and Protocols* 2012, 834:305-315.
10. Marks T, Sharp R: Bacteriophages and biotechnology: a review. *Journal of Chemical Technology and Biotechnology* 2000, 75(1):6-17.
11. Los M, Czyz A, Sell E, Wegrzyn A, Neubauer P, Wegrzyn G: Bacteriophage contamination: is there a simple method to reduce its deleterious effects in laboratory cultures and biotechnological factories? *Journal of applied genetics* 2004, 45(1):111-120.
12. Muthaiyan A, Limayem A, Ricke S C: Antimicrobial strategies for limiting bacterial contaminants in fuel bioethanol fermentations. *Progress in Energy and Combustion Science* 2011, 37(3):351-370.
13. Junker B, Lester M, Leporati J, Schmitt J, Kovatch M, Borysewicz S, Maciejak W, Seeley A, Hesse M, Connors N et al: Sustainable reduction of bioreactor contamination in an industrial fermentation pilot plant. *Journal of Bioscience and Bioengineering* 2006, 102(4):251-268.
14. Wang C C, Chang C W, Chu C P, Lee D J, Chang B V, Liao C S: Producing hydrogen from wastewater sludge by Clostridium bifermentans. *Journal of Biotechnology* 2003, 102(1):83-92.
15. Bachinger T, Riese U, Eriksson R K, Mandenius C F: Gas sensor arrays for early detection of infection in mammalian cell culture. *Biosensors & Bioelectronics* 2002, 17(5):395-403.
16. Young J H: STERILIZATION OF VARIOUS DIAMETER DEAD-ENDED TUBES. *Biotechnology and Bioengineering* 1993, 42(1):125-132.
17. Sharma M C, Gurtu A K: ASEPSIS IN BIOREACTORS. *Advances in Applied Microbiology, Vol* 39 1993, 39:1-27.
18. Bader F G: Sterilization: prevention of contamination. *Manual of industrial microbiology and biotechnology*/editors, Arnold L Demain and Nadine A Solomon: 345-362.
19. Bischoff K M, Liu S Q, Leathers T D, Worthington R E, Rich J O: Modeling Bacterial Contamination of Fuel Ethanol Fermentation. *Biotechnology and Bioengineering* 2009, 103(1):117-122.
20. Dearman B, Marschner P, Bentham R H: Methane production and microbial community structure in single-stage batch and sequential batch systems anaerobically co-digesting food waste and biosolids. *Applied Microbiology and Biotechnology* 2006, 69(5):589-596.
21. Burmolle M, Webb J S, Rao D, Hansen L H, Sorensen S J, Kjelleberg S: Enhanced biofilm formation and increased resistance to antimicrobial agents and bacterial invasion are caused by synergistic interactions in multi-species biofilms. *Applied and Environmental Microbiology* 2006, 72(6):3916-3923.
22. Brenner K, You L, Arnold F H: Engineering microbial consortia: a new frontier in synthetic biology. *Trends in Biotechnology* 2008, 26(9):483-489.
23. Fernandez A S, Hashsham S A, Dollhopf S L, Raskin L, Glagoleva O, Dazzo F B, Hickey R F, Criddle C S, Tiedje J M: Flexible community structure correlates with stable community function in methanogenic bioreactor communities perturbed by glucose. *Applied and Environmental Microbiology* 2000, 66(9):4058-4067.
24. Supaphol S, Jenkins S N, Intomo P, Waite I S, O'Donnell A G: Microbial community dynamics in mesophilic anaerobic co-digestion of mixed waste. *Bioresource Technology* 2011, 102(5):4021-4027.
25. Qian X D, Barlaz M A: Enumeration of anaerobic refuse-decomposing micro-organisms on refuse constituents. *Waste Management & Research* 1996, 14(2):151-161.
26. Tsavkelova E A, Netrusov A I: Biogas production from cellulose-containing substrates: A review. *Applied Biochemistry and Microbiology* 2012, 48(5):421-433.
27. Narihiro T, Sekiguchi Y: Microbial communities in anaerobic digestion processes for waste and wastewater treatment: a microbiological update. *Current Opinion in Biotechnology* 2007, 18(3):273-278.
28. Demirel B: Major Pathway of Methane Formation From Energy Crops in Agricultural Biogas Digesters. *Critical Reviews in Environmental Science and Technology* 2014, 44(3):199-222.
29. Manyi-Loh C E, Mamphweli S N, Meyer E L, Okoh A I, Makaka G, Simon M: Microbial Anaerobic Digestion (Bio-Digesters) as an Approach to the Decontamination of Animal Wastes in Pollution Control and the Generation of Renewable Energy. *International Journal of Environmental Research and Public Health* 2013, 10(9):4390-4417.
30. Liu F H, Wang S B, Zhang J S, Zhang J, Yan X, Zhou H K, Zhao G P, Zhou Z H: The structure of the bacterial and archaeal community in a biogas digester as revealed by denaturing gradient gel electrophoresis and 16S rDNA sequencing analysis. *Journal of Applied Microbiology* 2009, 106(3):952-966.
31. Zinder S H, Anguish T, Cardwell S C: Selective inhibition by 2-bromoethanesulfonate of methanogenesis from acetate in a thermophilic anaerobic digestor. *Appl Environ Microbiol* 1984, 47(6):1343-1345.
32. Jiang J G, Zhang Y J, Li K M, Wang Q, Gong C X, Li M L: Volatile fatty acids production from food waste: Effects of pH, temperature, and organic loading rate. *Bioresource Technology* 2013, 143:525-530.
33. Warnecke T, Gill R T: Organic acid toxicity, tolerance, and production in *Escherichia coli* biorefining applications. *Microbial Cell Factories* 2005, 4.
34. Babel S, Fukushi K, Sitanrassamee B: Effect of acid speciation on solid waste liquefaction in an anaerobic acid digester. *Water Research* 2004, 38(9):2417-2423.
35. Negri E D, Mataalvarez J, Sans C, Cecchi F: A MATHEMATICAL-MODEL OF VOLATILE FATTY-ACIDS (VFA) PRODUCTION IN A PLUG-FLOW REACTOR TREATING THE ORGANIC FRACTION OF MUNICIPAL SOLID-WASTE (MSW). *Water Science and Technology* 1993, 27(2):201-208.
36. Chen Y, Cheng J J, Creamer K S: Inhibition of anaerobic digestion process: A review. *Bioresource Technology* 2008, 99(10):4044-4064.
37. IndexMundi—Sugar Price [http://www.indexmundi.com/commodities/?commodity=sugar&months=60]
38. Center of Sustainable Systems UoM: Municipal Solid Waste Factsheet. Pub. No. CSS04-15. In.; 2014.
39. McCaskey T A, Zhou S D, Britt S N, Strickland R: BIOCONVERSION OF MUNICIPAL SOLID-WASTE TO LACTIC-ACID BY *LACTOBACILLUS* SPECIES. *Applied Biochemistry and Biotechnology* 1994, 45-6:555-568.
40. Yang S Y, Ji K S, Baik Y H, Kwak W S, McCaskey T A: Lactic acid fermentation of food waste for swine feed. *Bioresource Technology* 2006, 97(15):1858-1864.
41. Qin J, Zhao B, Wang X, Wang L, Yu B, Ma Y, Ma C, Tang H, Sun J, Xu P: Non-Sterilized Fermentative Production of Polymer-Grade L-Lactic Acid by a Newly Isolated Thermophilic Strain *Bacillus* sp 2-6. *Plos One* 2009, 4(2).
42. Watanabe M, Makino M, Kaku N, Koyama M, Nakamura K, Sasano K: Fermentative L-(+)-lactic acid production from non-sterilized rice washing drainage containing rice bran by a newly isolated lactic acid bacteria without any additions of nutrients. *Journal of Bioscience and Bioengineering* 2013, 115(4):449-452.
43. Datta R, Henry M: Lactic acid: recent advances in products, processes and technologies—a review. *Journal of Chemical Technology and Biotechnology* 2006, 81(7):1119-1129.
44. Markets Ma: Lactic Acid Market by Application (Biodegradable Polymer, Food & Beverage, Personal Care & Pharmaceutical) & Polylactic Acid Market by Application (Packaging, Agriculture, Automobile, Electronics, Textile) & Geography—Global Trends & Forecasts to 2019 In.; 2013.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. A method for producing lactic acid from organic waste, comprising
    contacting organic waste with a controlled microbial community to form a fermentation mixture,
    controlling the pH and temperature conditions of the controlled microbial community in the fermentation mixture, and
    fermenting the fermentation mixture under the controlled pH and temperature conditions for a time sufficient to produce lactic acid,
    wherein the controlled microbial community comprises Firmicutes, *Bacteroides* and *Spirochetes*,
    wherein the fermentation mixture has a solid content,
    wherein the pH is controlled to between 3.0 and 6.0,
    wherein the temperature is controlled to between 20° C. and 50° C., and
    wherein the method does not comprise sterilization of the organic waste.

2. The method of claim 1, wherein the method does not comprise enzyme addition to the fermentation mixture.

3. The method of claim 1, wherein the organic waste is food waste or agricultural waste.

4. The method of claim 1, wherein prior to fermentation, the organic waste is mechanically disrupted to a particle size of approximately 1 mm or smaller.

5. The method of claim 4, wherein the mechanical disruption comprises shredding or grinding.

6. The method of claim 1, wherein the pH is adjusted by addition of sodium hydroxide or other bases.

7. The method of claim 1, wherein the temperature of the fermentation mixture is about 37° C.

8. The method of claim 1, further comprising shifting the pH to between pH 3.86 and pH 4.75, inclusive, at or near the end of fermentation.

9. The method of claim 1, wherein 60-100 grams of lactic acid per liter is produced.

10. The method of claim 1, wherein the pH is adjusted to between pH 5.0 to pH 6.0.

11. The method of claim 10, wherein the pH is adjusted to about pH 5.5.

12. The method of claim 1, wherein the pH is controlled to be at or below 6.0 and above the pKa of lactic acid.

13. A method for producing lactic acid from organic waste, comprising
    contacting organic waste with a controlled microbial community to form a fermentation mixture,
    controlling the pH and temperature conditions of the controlled microbial community in the fermentation mixture, and
    fermenting the fermentation mixture under the controlled pH and temperature conditions for a time sufficient to produce lactic acid,
    wherein the controlled microbial community comprises Firmicutes, *Bacteroides* and *Spirochetes*,
    wherein the fermentation mixture has a solid content,
    wherein the temperature is controlled to between 20° C. and 50° C., and
    wherein the pH is controlled to be at or below 6.0 and above the pKa of lactic acid.

14. The method of claim 13, wherein at least 60 or more grams of lactic acid per liter are produced.

15. The method of claim 13, wherein 60-100 grams of lactic acid per liter or 60-150 grams of lactic acid per kilogram of organic waste is produced.

16. A method for producing lactic acid from organic waste, comprising
   contacting organic waste with a controlled microbial community to form a fermentation mixture,
   controlling the pH and temperature conditions of the controlled microbial community in the fermentation mixture, and
   fermenting the fermentation mixture under the controlled pH and temperature conditions for a time sufficient to produce lactic acid,
   wherein the controlled microbial community comprises *Firmicutes, Bacteroides* and *Spirochetes,*
   wherein the fermentation mixture has a solid content,
   wherein the pH is controlled to between 3.0 and 6.0,
   wherein the temperature is controlled to between 20° C. and 50° C., and
   wherein 60 or more grams of lactic acid per liter are produced.

17. The method of claim 16, wherein 60-100 grams of lactic acid per liter or 60-150 grams of lactic acid per kilogram of organic waste is produced.

18. The method of claim 17, wherein the organic waste is food waste.

* * * * *